US00PP13412P3

(12) United States Plant Patent
Mellichamp et al.

(10) Patent No.: US PP13,412 P3
(45) Date of Patent: Dec. 24, 2002

(54) SARRACENIA PITCHER PLANT NAMED 'REDBUG'

(75) Inventors: T. Lawrence Mellichamp, Charlotte, NC (US); Robert K. Gardner, Chapel Hill, NC (US)

(73) Assignees: University of North Carolina at Charlotte, Charlotte, NC (US); University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/755,823

(22) Filed: Jan. 5, 2001

(65) Prior Publication Data

US 2002/0129411 P1 Sep. 12, 2002

(51) Int. Cl.[7] ..... A01H 5/00
(52) U.S. Cl. ..... Plt./263
(58) Field of Search ..... Plt./263

(56) References Cited

PUBLICATIONS

Mellichamp and Gardner (Jun. 1987) New cultivars of Sarracenia. *Carnivorous Plant Newsletter,* 16:39–42.

D'Amato, P. The American Pitcher Plants. In: The Savage Garden. Ten Speed Press, California. 1998. p. 70–102.

D'Amato, P. The Sun Pitchers. In: The Savage Garden. Ten Speed Press, California. 1998. p. 110–118.

D'Amato, P. The West Australian Pitcher Plant. In: The Savage Garden. Ten Speed Press, California. 1998. p. 168–173.

D'Amato, P. The Tropical Pitcher Plants. In: The Savage Garden. Ten Speed Press, California. 1998. p. 236–281.

*NCBG Plant Records: Sarracenia×'Redbug.'* New Accessions Form and Tables. Dec. 13, 2000.

*Primary Examiner*—Bruce R. Campell
*Assistant Examiner*—Susan B. McCormick
(74) *Attorney, Agent, or Firm*—Myers Bigel Sibley & Sajovec, P.A.

(57) ABSTRACT

A new and distinct cultvar of Sarracenia called 'Redbug' is described that is a vigorously growing, compact plant having pubescent dark Chrysanthemum Crimson (H.C.C. #824) pitchers, suffused with veins of a deeper cast of Chrysanthemum Crimson. The pitcher is distinguished from other Sarracenia by having a higher width-to-length ratio, a wider hood, and a prominent horizontal filament. Furthermore, in the winter the leaves retain color and texture when grown outdoors in United States Department of Agriculture Hardiness Zone 8 or warmer (minimum winter temperature to 10° F.).

1 Drawing Sheet

LATIN NAME OF THE GENUS AND SPECIES

The Latin name of the novel hybrid plant variety disclosed herein is *Sarracenia rubra* ssp. *wherryi*×*Sarracenia rubra* ssp. *rubra.*

VARIETY DENOMINATION

The inventive cultivar of Sarracenia disclosed herein has been given the variety denomination 'Redbug'.

BACKGROUND OF THE INVENTION

Sarracenia species are long-lived, herbaceous, perennial, insectivorous plants found growing in open, sunny, moist meadows or long-leaf pine savannas predominantly found throughout the southeastern United States. The plants produce pitchers which are hollow, modified leaves. Each pitcher has a hood, which typically covers the mouth of the pitcher to keep rainwater out and insect prey trapped inside. Insects are attracted by the color of the pitchers, the nectar produced around the mouth of the pitcher, and the smell of decaying insects within the pitcher. The ability to absorb nutrients from digested insect prey has been shown to supply necessary nourishment to the roots, stems, and leaves of Sarracenia spp.; and may account for the ability of these plants to thrive predominantly in nutrient-poor acidic soils characteristic of the southeastern United States.

Sarracenia pitcher plants have been of horticultural interest for well over one-hundred years. One problem in the production of commerically-available Sarracenia pitcher plants is the lack of identified horticulturally superior plants. To meet the current demand, wild species are being harvested, resulting in a depletion of native populations. There are approximately eight species found in the wild, and these species can cross-pollinate to produce fertile hybrids that grow well in cultivation. Therefore, it would be desirable to produce new, more robust cultivars of pitcher plants with enhanced characteristics such as compact growth, colorful leaves, and winter foliage to meet the current horticultural demand.

BRIEF SUMMARY OF THE INVENTION

The present Sarracenia 'Redbug' hybrid plant (*Sarracenia rubra* ssp. *wherryi*×*Sarracenia rubra* ssp. *rubra*) is a dwarf cultivar with pitcher leaves that are distinctly widened gradually above the middle, then narrowed somewhat at the mouth of the pitcher. The plant has dark Chrysanthemum Crimson (Horticultural Color Chart (H.C.C.). #824) tubular leaves, suffused with veins of a deeper cast of Chrysanthemum Crimson (H.C.C. #824). The pitcher leaves are thick, have very fine but distinct fuzz covering the entire surface, have a width-length ratio of 0.1, and prolonged retention of foliage with attractive leaf color during the dormant season.

The hood of Sarracenia 'Redbug' completely covers and extends beyond the leaf orifice and often has a slightly scalloped or wavy margin, and a prominent horizontal filament at its tip up to 2 mm long. Furthermore, this plant is a vigorous, compact grower (short in stature with many pitchers), forming a clump from a single crown in one growing season with flushes of new pitchers being produced all summer.

Lineage: The 'Redbug' cultivar originated as a single hybrid seedling at the North Carolina Botanical Garden, part of the University of North Carolina at Chapel Hill, in the late 1980s. 'Redbug' is a hybrid derived from a cross of *Sarracenia rubra* subspecies *rubra* (a native dwarf pitcher plant from coastal North Carolina) and *Sarracenia rubra* subspecies *wherryi*, a native species from southeastern Alabama. In 1990, the single individual plant now known as 'Redbug' was selected because of its multitude of exceptional features, and has been propagated asexually since that time. While each parental species had only a subset of horticulturally desirable features, 'Redbug' attained the full composite of features including vibrant color, compact growth, and winter foliage retention. It showed exceptional hybrid vigor and grew well under a variety of conditions.

Asexual reproduction: Sarracenia 'Redbug' was first asexually reproduced at the North Carolina Botanical Garden in Chapel Hill, N.C. by division of the rhizome, i.e., clump divison, in 1990. The combination of characteristics disclosed herein for Sarracenia 'Redbug' is stable through successive generations of asexual reproduction.

DETAILED BOTANICAL DESCRIPTION

Figure 1:
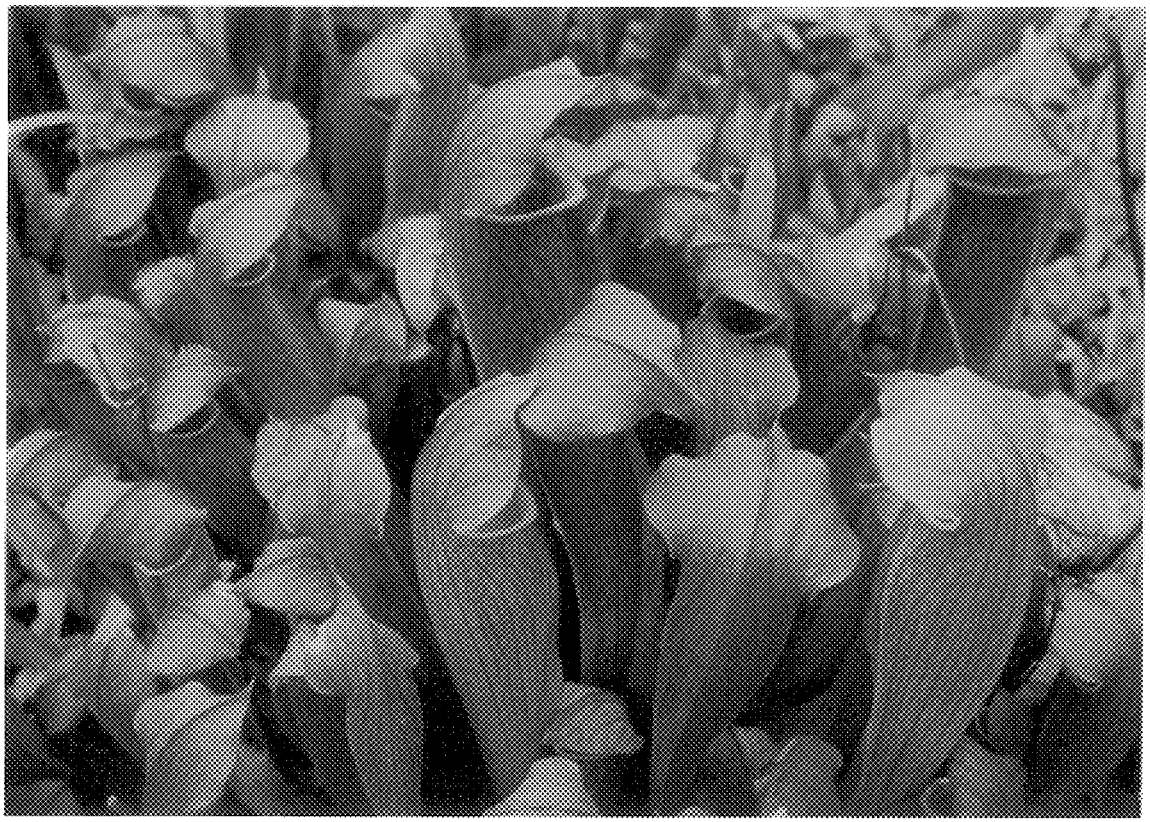
FIG. 1 is a color photograph of a typical specimen of the Sarracenia 'Redbug' hybrid in the summer receiving full sunlight. Leaves at various stages of development are presented.

The following is a detailed description of the botanical characteristics of a new and distinct cultivar of Sarracenia plant known by the cultivar name 'Redbug', and botanically known as *Sarracenia rubra* ssp. *wherryi*×*Sarracenia rubra* ssp. *rubra*. All colors cited herein refer to the Horticultural Colour Chart (H.C.C.) designations, issued by The British Colour Council in collaboration with The Royal Horticultural Society. Where dimensions, sizes, colors and other characteristics are given, it is to be understood that such characteristics are approximations or averages set forth as accurately as practicable. The descriptions reported herein are from mature specimens that were at least 12 years old and grown outdoors in full sunlight in Chapel Hill, N.C. or Charlotte, N.C. unless otherwise noted. 'Redbug' has not been observed under all possible environmental conditions. The appearance may vary with variations in the environment such as temperature, light intensity, day length, cultural conditions, and the like.

Growth conditions: Sarracenia 'Redbug' is a strong grower and adaptable to pot culture. It prefers 100% full sunlight and warm temperatures to bring out the deepest cast of Chrysanthemum Crimson (H.C.C. #824). While new pitcher leaves may be Scheele's Green (H.C.C #860) at first, they become a cardinal Red (H.C.C. #822) color as the leaves develop into mature pitchers (within 3–4 weeks). This trait is most similar to the *S. rubra* ssp. *rubra* parent. 'Redbug' prefers an acidic, peat-based, constantly-moist soil.

During the winter (or under similar day length and temperature conditions as experienced during winter), there is a prolonged retention of foliage, and the leaves maintain color and a fuzzy texture. 'Redbug' is hardy to United States Department of Agriculture Hardiness Zone 6 (or colder). The pitchers eventually die down after the prolonged rigors of winter weather, but new growth resumes in early to mid-Spring (April in Chapel Hill and Charlotte, N.C.) Typical of the *S. rubra* ssp. *rubra* complex, new growth (i.e., new leaves and short growth of the rhizome) continues strongly all summer, stopping in mid-Autumn (October in Chapel Hill and Charlotte, N.C.).

Vegetative structures: Sarracenia 'Redbug' is a clump-forming herbaceous perennial, growing from a horizontal rhizome that is typically approximately 5 mm in diameter and up to several centimeters long. Typically, thick white roots grow from the base of newer leaves. A cluster of tubular pitcher leaves arises from the growing tip of the rhizome. The leaves, at maturity, curve slightly forward and range from 15–25 cm tall, with a diameter at the widest point of 1.8–2.8 cm. Sarracenia 'Redbug' has a wide pitcher for its length (FIG. 1). The pitcher averages a width-to-length ratio of 0.1, which is approximately twice the width-to length ratios of the parents. A hood covers and extends beyond the orifice of the pitcher, and often has a wavy or slightly scalloped margin. There are no long hairs on the under surface of the hood. The hood measures up to 4.0 cm wide and 4.0 cm long, which is approximately two-times the size of the hood for the parent species. The tip of the hood forms a prominent filament up to 2.0 mm long, usually held horizontally. The leaves are of thick texture, and finely pubescent (like the *S. rubra* ssp. *wherryi* parent) on the outside. The rim of the orifice (pitcher mouth) is thick and revolute. There is a typical wing (flattened flange of tissue) along the front side of the summer-produced pitcher along its entire length, up to 0.5 cm wide (up to 1.5 cm wide on young spring leaves) that is the same color as the tube. Furthermore, there are no winter phyllodia (non-pitcher leaves) produced by 'Redbug' as may be found in some species not in the *Sarracenia rubra* complex (for example, in *S. flava, S. leucophylla*, and *S. oreophylla*, and their hybrids).

Pitcher leaf coloration: FIG. 1 shows the distinctive coloration of a typical 'Redbug' specimen in the summer and in full sun. The rim of the orifice is dark Chrysanthemum Crimson (H.C.C #824) on the front portion and Sap Green (H.C.C. #62) on the back portion. The rim of the *S. rubra* ssp. *rubra* parent is Currant Red (H.C.C. #821) all around; the *S. rubra* ssp. *wherryi* parent is Sap Green (H.C.C. #62) all around the rim. The upper three-quarters of a mature 'Redbug' pitcher tube is Chrysanthemum Crimson (H.C.C. #824) and the lower quarter is Scheele's Green (H.C.C. #860). The veins on the upper pitcher form a distinct reticulate pattern on the outside and are seen as a deep cast of Chrysanthumum Crimson (H.C.C. #824).

Variations in color: In full sunlight conditions, the pitcher color starts out as Scheele's Green (H.C.C. #860) suffused with a light cast of Chrysanthemum Crimson (H.C.C. #824) in the immature pitcher, which develops into a deeper cast of Chrysanthemum Crimson (H.C.C. #824) in the mature pitcher. Similar to other species of Sarracenia, 'Redbug' will not robustly develop distinct pitchers under light intensity conditions of 50% or less, and the leaves typically remain Scheele's Green (H.C.C. #860) suffused with a light cast of Chrysanthemum Crimson (H.C.C. #824) under these conditions. In the summer, the upper three-quarters of the pitcher tube is Chrysanthemum Crimson (H.C.C. #824) and the lower quarter of the pitcher is Scheele's Green (H.C.C. #860) (FIG. 1). It will be appreciated by those skilled in the art that plants grown in less than ideal lighting and moisture conditions will display pitchers that are different in size, shape and color from the typical specimen described here. In the winter, the entire pitcher retains a Garnet Brown (H.C.C. #918) color.

Reproductive structures: In the late spring (late April to mid-May in Chapel Hill and Charlotte, N.C.) solitary, nodding flowers develop on a scape (stems with single flowers). There may be 1–3 scapes produced by each growing point, a trait unique to the *S. rubra* complex. Flowers are typically about 4–5 cm in diameter, and they naturally hang upside-down with petals hanging down. A single flower has 5 sepals, 5 petals, many stamens, and 5 stigmas on an expanded umbrella-like style. The sepals are thick textured (they persist until the seed pod ripens in late summer; September in Chapel Hill and Charlotte, N.C.) 2.5 cm long and 1.5 cm wide in the middle, tapering at each end to rounded tips. They are similar in color to the petals (Oxblood Red [H.C.C. #823], often with some Scheele's Green [H.C.C. #860]). Below the 5 sepals are three small round-tipped Oxblood Red (H.C.C. #823) bracts (leaf-like structures) that are 0.5–0.75 cm long. Flower petals are Rose Bengal (H.C.C. #25), Cardinal Red (H.C.C. #822) to Oxblood Red (H.C.C. #823) in color. The petals are thin textured, 3 cm long, spatula-shaped; the rounded terminal third is 1.5–2 cm wide, the middle portion is 0.5 cm wide, and the basal third is 1 cm wide. The margin is smooth to slightly wavy, and the surface is smooth. The flowers are typical of other members of the *S. rubra* ssp. *rubra* complex (which includes both parents) and cannot be used to separate sub-species or hybrids. Pollination by bumblebees results in numerous (up to 500) seeds produced in a rounded capsule (seed pod) 1 cm wide. Each seed is 2 mm long and 1 mm wide, Yellow-ochre (H.C.C. #70) in color, with a rough surface texture. They are generally smaller than seeds of other Sarracenia species.

Comparison with other Sarracenia cultvars: Sarracenia 'Redbug' differs from most other tall species of Sarracenia in that it is more compact (maximum leaf height of 25 cm compared to 91–122 cm for other tall, slender species) and is more vigorous in its growth (producing multiple flushes of pitchers in a single growing season compared to a single flush produced by most other species, when undisturbed). The pitcher of *S. rubra* ssp. *rubra* typically has more Currant Red (H.C.C. #821) coloration or, often, Scheele's Green (H.C.C. #860) with Currant Red (H.C.C. #821) veins, and *S. rubra* ssp. *wherryi* typically is Scheele's Green (H.C.C. #860) with Currant Red (H.C.C. #821) veins, whereas the pitcher of Sarracenia 'Redbug' is a uniform deep cast of Chrysanthemum Crimson (H.C.C. #860) in mature, sun-grown leaves. In less light, the mature 'Redbug' pitchers will have more Scheele's Green (H.C.C. #860) color with Currant Red (H.C.C. #821) veins rather than a solid Chrysanthemum Crimson (H.C.C. #860) color. A typical 'Redbug' plant will, like the *S. rubra* ssp. *wherryi* parent, produce continuous flushes of leaves in a single summer season versus other pitcher plants which typically produce a single flush in a season. It differs from its *S. rubra* subspecies *rubra* parent in many aspects (see TABLE 1), including: 1) it has a distinctly fatter tube, particularly towards its apex (up to 2.5 cm in diameter verses 1.25 cm in diameter), 2) its hood is three times wider, 3) it has a more clumped appearance, and 4) it has a distinct coating of short fine hairs on the outer surface of the leaf giving it a 'fuzzy' feel and appearance. In addition to color differences, it may be distinguished from its other parent, *S. rubra* ssp. *wherryi*, in having a hood that is more than 1.5 times wider and a tube that is two times wider (TABLE 1). 'Redbug' also has a prominent filament formed at the tip of the hood, typically held horizontally, whereas in the *S. rubra* ssp. *wherryi* parent the filament is generally reflexed and held in a vertical position, and the filament is only very small or even absent in the *S. rubra* ssp. *rubra* parent. The fowers do not differ from any of the forms of *S. rubra* ssp. *wherryi.*

Sarracenia 'Redbug' differs from all other hybrids in its combination of color, stature, texture, pitcher and hood shape, vigor and winter appearance.

TABLE 1

| Characteristic | *S. rubra* ssp. rubra | *S. rubra* ssp. wherryi | Sarracenia 'Redbug' |
|---|---|---|---|
| Leaf Length | 140 mm | 156 mm | 190 mm |
| Diameter of Leaf at Widest Point* | 8.2 mm | 9.0 mm | 20.1 mm |
| Leaf Width to Leaf Length Ratio | 0.059 | 0.058 | 0.106 |
| Hood Width | 11.2 mm | 17.3 mm | 28.3 mm |
| Hood Filament (Tip) | minuscule to absent | 1–2 mm reflexed, typically vertical | 1–2 mm prominent, typically horizontal |

All data are averaged from 10 random measurements collected from mature plants in December 2000 at the North Carolina Botanical Garden where the plants were grown in full sunlight outdoors.
Note that the data in this table are not typical of summer pitchers, although the relative sizes provided are helpful for differentiation of 'Redbug' from the parent plants.
*not to be confused with orifice diameter.

What is claimed is:

1. A new and distinct cultivar of Sarracenia plant named 'Redbug', substantially as illustrated and described herein.

* * * * *